United States Patent
Levene et al.

(10) Patent No.: US 9,012,857 B2
(45) Date of Patent: Apr. 21, 2015

(54) MULTI-LAYER HORIZONTAL COMPUTED TOMOGRAPHY (CT) DETECTOR ARRAY WITH AT LEAST ONE THIN PHOTOSENSOR ARRAY LAYER DISPOSED BETWEEN AT LEAST TWO SCINTILLATOR ARRAY LAYERS

(75) Inventors: Simha Levene, Hanegev (IL); Nicolaas Johannes Anthonius Van Veen, Geldrop (NL); Amiaz Altman, Tel Aviv (IL); Igor Uman, Zichron Yaakov (IL); Rafael Goshen, Haifa (IL)

(73) Assignee: Koninklijke Philips N.V., Eindhoven (NL)

( * ) Notice: Subject to any disclaimer, the term of this patent is extended or adjusted under 35 U.S.C. 154(b) by 242 days.

(21) Appl. No.: 13/465,560

(22) Filed: May 7, 2012

(65) Prior Publication Data

US 2013/0292574 A1   Nov. 7, 2013

(51) Int. Cl.
| | |
|---|---|
| G01T 1/20 | (2006.01) |
| G01T 1/00 | (2006.01) |
| G01T 1/202 | (2006.01) |
| G01T 1/36 | (2006.01) |
| A61B 6/00 | (2006.01) |
| A61B 6/03 | (2006.01) |

(52) U.S. Cl.
CPC .............. *G01T 1/2018* (2013.01); *A61B 6/482* (2013.01); *A61B 6/032* (2013.01); *G01T 1/202* (2013.01); *G01T 1/362* (2013.01)

(58) Field of Classification Search
CPC ...... A61B 6/482; A61B 6/032; G01T 1/2018; G01T 1/362; G01T 1/202; H01L 27/14663
USPC .......... 250/370.09, 370.11, 366; 378/19, 18, 378/98.9
See application file for complete search history.

(56) References Cited

U.S. PATENT DOCUMENTS

| | | | |
|---|---|---|---|
| 4,945,243 A | 7/1990 | Arques | |
| 5,138,167 A * | 8/1992 | Barnes | 250/370.01 |
| 5,825,032 A * | 10/1998 | Nonaka et al. | 250/370.09 |
| 6,049,074 A * | 4/2000 | Endo et al. | 250/208.1 |
| 7,435,965 B2 * | 10/2008 | Fuchs et al. | 250/367 |
| 7,606,347 B2 * | 10/2009 | Tkaczyk et al. | 378/19 |
| 7,968,853 B2 | 6/2011 | Altman et al. | |
| 8,791,537 B2 * | 7/2014 | Chan et al. | 257/436 |
| 2003/0016779 A1 * | 1/2003 | Pohan et al. | 378/19 |
| 2004/0113085 A1 * | 6/2004 | Heismann et al. | 250/370.09 |
| 2005/0111613 A1 | 5/2005 | Mliner et al. | |
| 2007/0158573 A1 * | 7/2007 | Deych | 250/370.11 |
| 2008/0011960 A1 * | 1/2008 | Yorkston et al. | 250/370.09 |
| 2008/0061395 A1 * | 3/2008 | Tkaczyk et al. | 257/443 |
| 2008/0210877 A1 * | 9/2008 | Altman et al. | 250/366 |
| 2009/0121146 A1 * | 5/2009 | Luhta et al. | 250/370.11 |
| 2010/0102242 A1 | 4/2010 | Burr et al. | |

(Continued)

FOREIGN PATENT DOCUMENTS

| | | |
|---|---|---|
| IL | 165619 A | 3/2012 |
| JP | 2011019891 | 3/2011 |

*Primary Examiner* — Yara B Green

(57) ABSTRACT

An imaging system (100) includes a radiation sensitive detector array (110). The detector array includes at least two scintillator array layers (116). The detector array further includes at least two corresponding photosensor array layers (114). At least one of the at least two photosensor array layers is located between the at least two scintillator array layers in a direction of incoming radiation. The at least one of the at least two photosensor array layers has a thickness that is less than thirty microns.

22 Claims, 8 Drawing Sheets

(56) References Cited

U.S. PATENT DOCUMENTS

2010/0108893 A1* 5/2010 Flitsch et al. ............. 250/361 R
2011/0226951 A1* 9/2011 Kammerer et al. ........ 250/336.1
2012/0106698 A1* 5/2012 Karim et al. .................... 378/37
2012/0205544 A1* 8/2012 Nakatsugawa et al. ....... 250/367

* cited by examiner

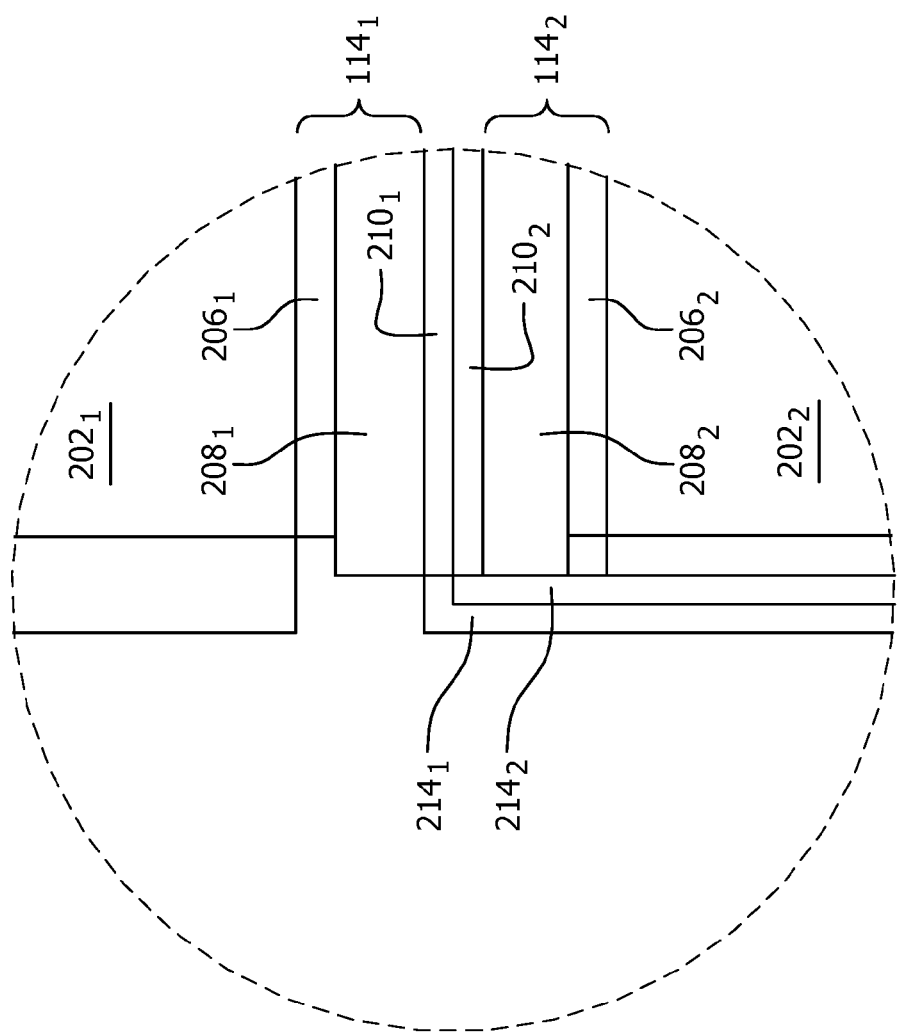
FIG. 2-II

MULTI-LAYER HORIZONTAL COMPUTED TOMOGRAPHY (CT) DETECTOR ARRAY WITH AT LEAST ONE THIN PHOTOSENSOR ARRAY LAYER DISPOSED BETWEEN AT LEAST TWO SCINTILLATOR ARRAY LAYERS

The following generally relates to a multi-layer CT detector array and more particularly to a multi-layer horizontal CT detector array with at least one thin photosensor array layer disposed between at least two scintillator array layers.

A typical CT scanner includes a radiation source that rotates about and emits radiation that traverses an examination region and a radiation-sensitive detector array which detects the radiation that traverses the examination region. The detector array has included a scintillator array coupled to a photosensor array. The scintillator array receives the radiation and converts it to light, and the photosensor array receives the light and produces an electrical signal indicative thereof. The signal can be reconstructed to generate volumetric image data.

A dual-energy (also known as a double decker) detector array includes two pairs of scintillator/photosensor arrays. Generally, one of the scintillator/photosensor array pairs mainly detects lower energy radiation and the other of the scintillator/photosensor array pairs mainly detects higher energy radiation. In a "horizontal" configuration, the photosensor arrays extend in a transverse direction, which is perpendicular to the direction of the incoming radiation. In a "vertical" configuration, the photosensor arrays extend in the direction of the incoming radiation.

U.S. Pat. No. 7,968,853 describes a vertical double decker detector. This detector includes a plurality of modules that extend along the z-axis and are arranged along the transverse direction. Each module includes two sticks of scintillator rows mounted to a photodiode array strip. The first stick has a lower-Z material and is arranged on the strip in connection with a first photodiode array row so that is it closer to the incoming radiation. The second stick has a higher-Z material and is arranged on the strip in connection with a second photodiode array row so that it is farther from the incoming radiation.

Several of these strips are successively mounted on a substrate of the module and are successively coupled to readout electronics on an opposing side of the substrate. Unfortunately, the assembly of the strips and a single module requires numerous operations, which are tedious and consume time. The "horizontal" geometry uses only two (2) two dimensional scintillator arrays which are respectively coupled to two (2) two dimensional photodiode arrays. As such, the assembly of a horizontal detector requires fewer operations than the assembly of the vertical detector, is less costly, and is more precise.

However, with the "horizontal" geometry, one or both of the two dimensional photodiode arrays is exposed to about 50% of the x-ray beam flux, some of which it absorbs. Unfortunately, the absorbed flux may undergo direct-conversion, producing direct-conversion current, which may introduce direct-conversion noise into the measured data. This may result in reduced image quality, for example, reduced spectral resolution.

Aspects described herein address the above-referenced problems and/or others.

In one aspect, an imaging system includes a radiation sensitive detector array. The detector array includes at least two scintillator array layers. The detector array further includes at least two corresponding photosensor array layers. At least one of the at least two photosensor array layers is located between the at least two scintillator array layers in a direction of incoming radiation. The at least one of the at least two photosensor array layers has a thickness that is less than thirty microns.

In another aspect, a method includes detecting radiation with a multi-spectral horizontal detector array of an imaging system, generating a signal, via the detector array, indicative of the detected radiation; and processing the signal to generate one or more images. The detector array includes at least two scintillator array layers and at least two corresponding photosensor array layers. The at least one of the at least two photosensor array layers has a thickness that is less than thirty microns.

In another aspect, a radiation sensitive detector array includes at least two scintillator array layers and at least two corresponding photosensor array layers. At least one of the at least two photosensor array layers is located between the at least two scintillator array layers in a direction along incoming radiation. The at least one of the at least two photosensor array layers has a thickness less than thirty microns.

The invention may take form in various components and arrangements of components, and in various steps and arrangements of steps. The drawings are only for purposes of illustrating the preferred embodiments and are not to be construed as limiting the invention.

FIG. 1 schematically illustrates an example imaging system that includes a multi-spectral imaging detector.

Figure 4:
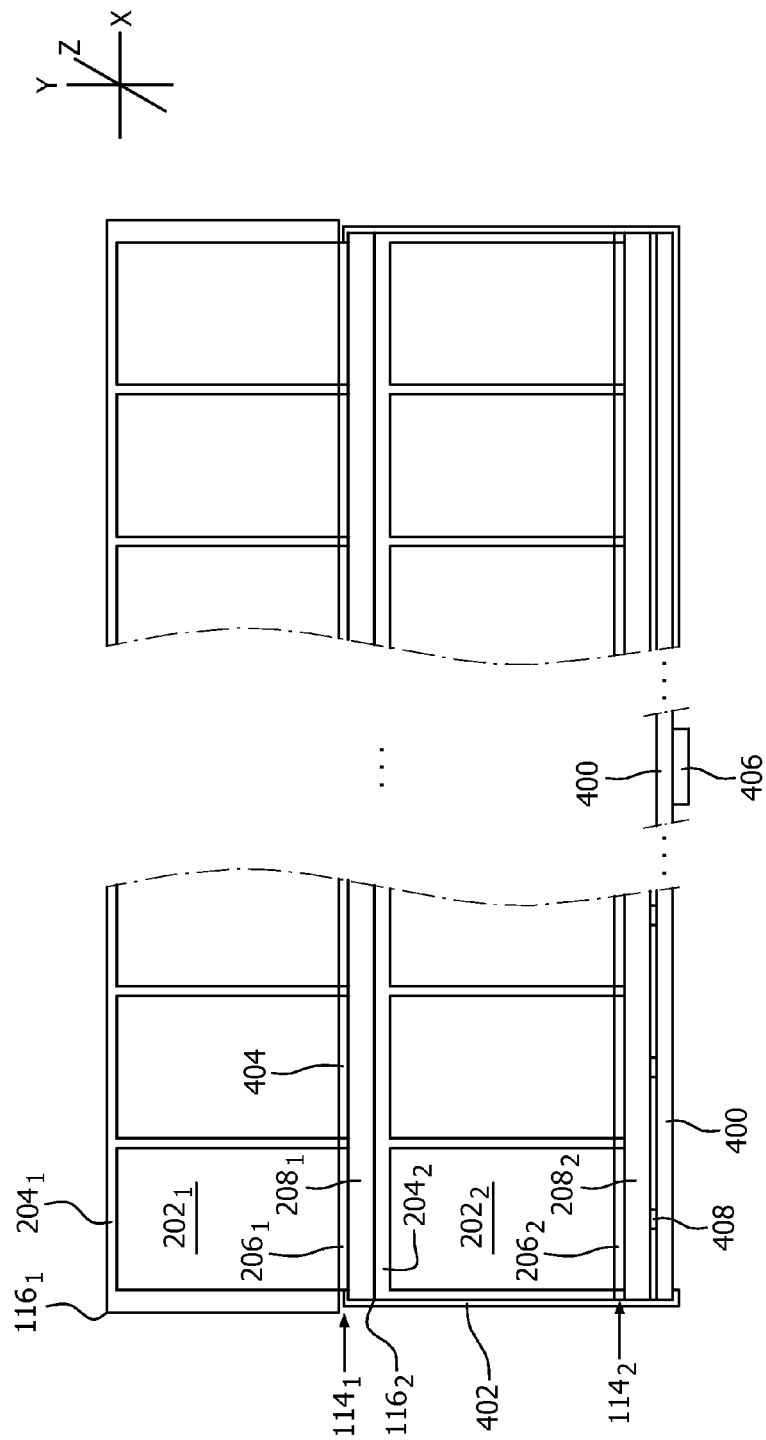

FIG. 4 schematically illustrates an alternative approach for routing electrical signal in connection with the multi-spectral imaging detector.

Figure 5:
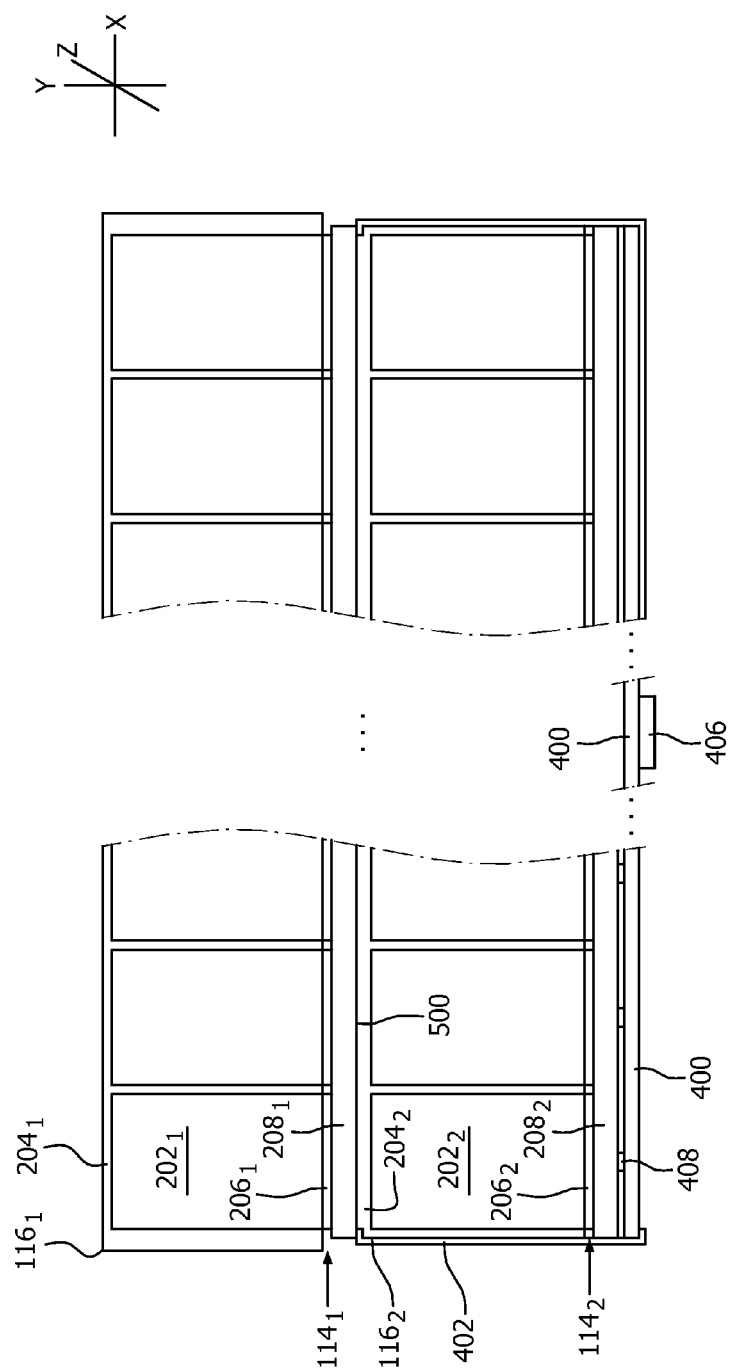

FIG. 5 schematically illustrates another alternative approach for routing electrical signal in connection with the multi-spectral imaging detector.

Figure 6:
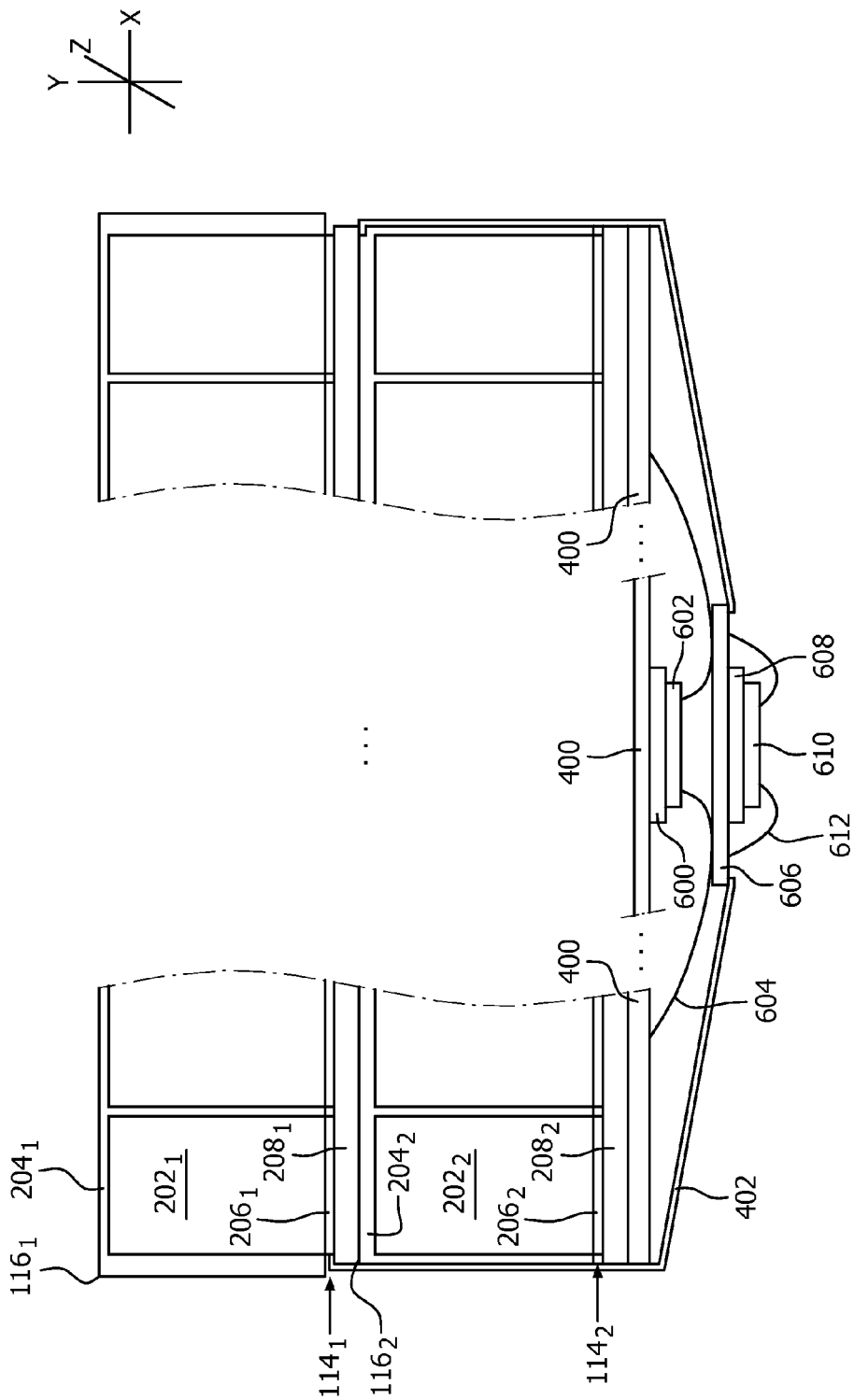

FIG. 6 schematically illustrates an alternative approach for mounting readout electronics.

Figure 7:
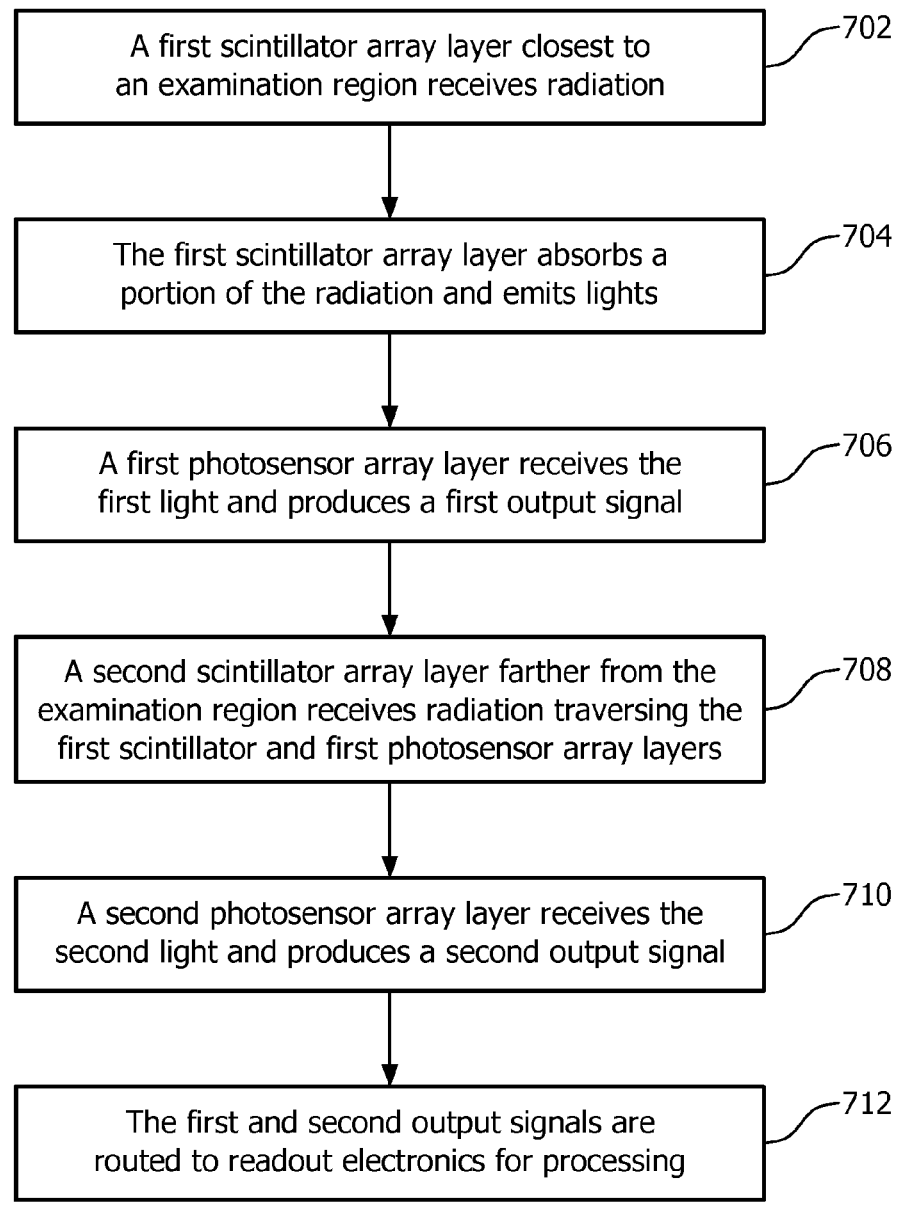

FIG. 7 illustrates a method of using the multi-spectral imaging detector.

Figure 1:
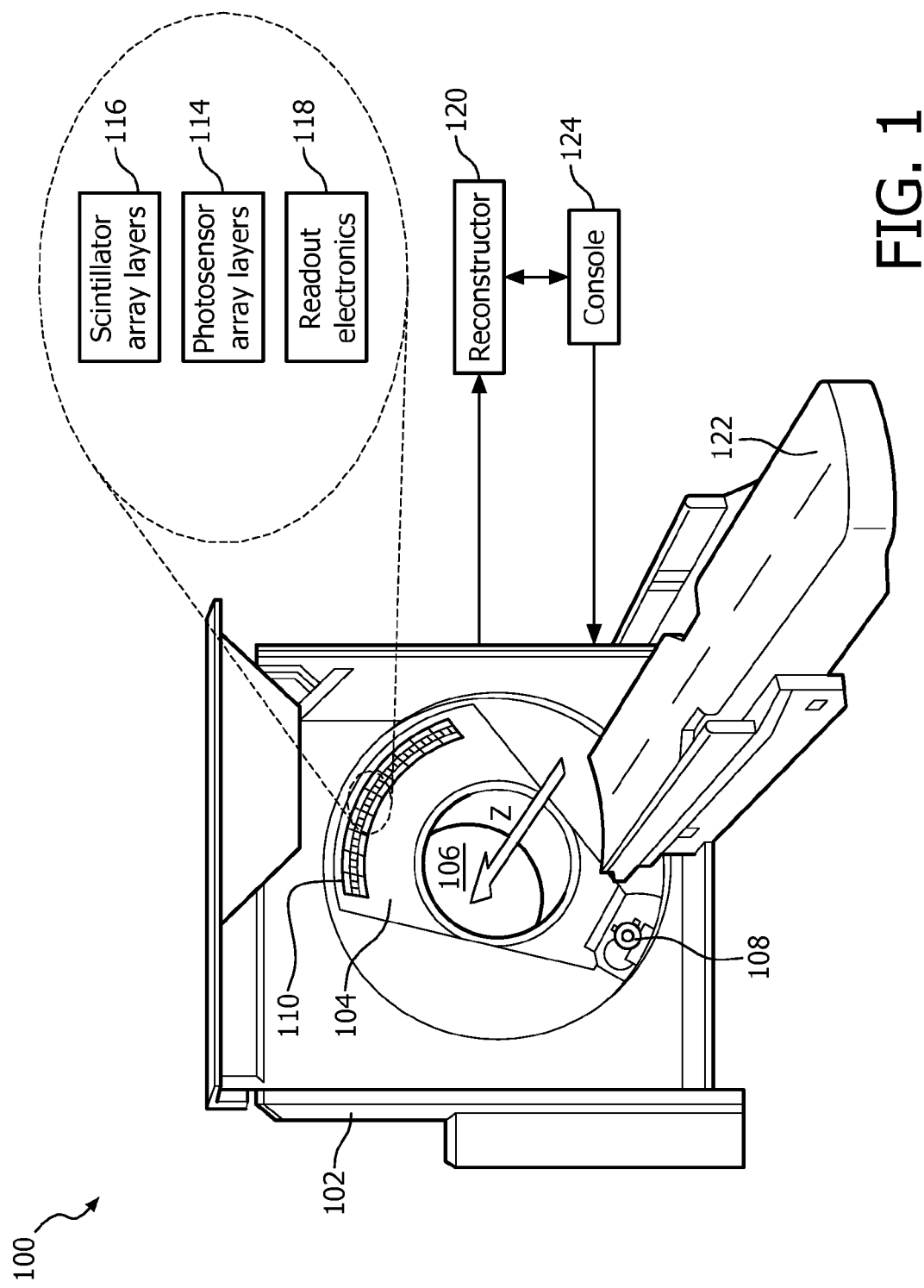

Initially referring to FIG. 1, an imaging system 100 such as a computed tomography (CT) scanner is illustrated. The imaging system 100 includes a generally stationary gantry 102 and a rotating gantry 104, which is rotatably supported by the stationary gantry 102. The rotating gantry 104 rotates around an examination region 106 about a longitudinal or z-axis. A radiation source 108, such as an x-ray tube, is supported by and rotates with the rotating gantry 104, and emits radiation (e.g., x-ray photons) that traverses the examination region 106.

A radiation sensitive detector array 110 is affixed to the rotating gantry 104 and subtends an angular arc, across from the radiation source 108, opposite the examination region 106. The illustrated detector array 110 is a multi-layer horizontal detector array 110 with N scintillator array layers 116 (where N is an integer greater than one), M photosensor array layers 114 (where M is an integer greater than one), and readout electronics 118. As described in greater detail below, in one instance, at least one of the photosensor array layers 114 is located between at least two of the scintillator array layers 116.

In the illustrated embodiment, the at least one of the photosensor array layers 114 has the following x-ray attenuation characteristic: substantially all x-ray photons incident thereon will traverse the at least one of the photosensor array layers 114 and will not interact with the at least one of the photosensor array layers 114 to produce more than a predetermined threshold about of direct-conversion current via direct-conversion. For example, the predetermined threshold can be less than ten percent, less than five percent, less than one percent, less than a half a percentage, and/or less than another percent.

An example of the at least one of the photosensor array layers 114 is a thin layer of material, for example, a layer having a thickness of thirty microns (300 or less. Another example of the at least one of the photosensor array layers 114 is a layer of a lower atomic number (Z) material, with a Z equal to or less than thirty-five. Another example of the at least one of the photosensor array layers 114 is a layer of organic photosensor; these have very low Z, and correspondingly low absorption of x-rays. Such a photosensor array layer may have a higher detection quantum efficiency (DQE), relative to a vertical detector array, for example, because of greater detection surface area, and this allows for lower dose scans and/or improved image quality.

The radiation sensitive detector array 110, in response to detecting x-ray photons, generates a signal indicative of the detected radiation. Readout electronics 118 process the signal and output the processed signal. Spectral information can be obtained by processing the signals output by the different photosensor array layers, and conventional (non-spectral) information can be obtained by summing the outputs signals of different photosensor array layers corresponding to the same ray path.

A reconstructor 120 reconstructs the signal using a spectral or conventional reconstruction algorithm, and generates volumetric image data. One or more spectral or conventional images can be generated from the volumetric image data. A subject support 122, such as a couch, supports an object or subject in the examination region 106. The support 122 may be movable along the x, y and z-axes in coordination with the rotation of the rotating gantry 104 to facilitate helical, axial, or other desired scanning trajectories.

A general purpose computing system serves as an operator console 124, which includes human readable output devices such as a display and/or printer and input devices such as a keyboard and/or mouse. The console 124 allows an operator to control an operation of the system 100, for example, by allowing the operator to select a spectral or conventional scan protocol, a spectral and/or conventional reconstruction algorithm, initiate scanning, etc.

Figure 2:
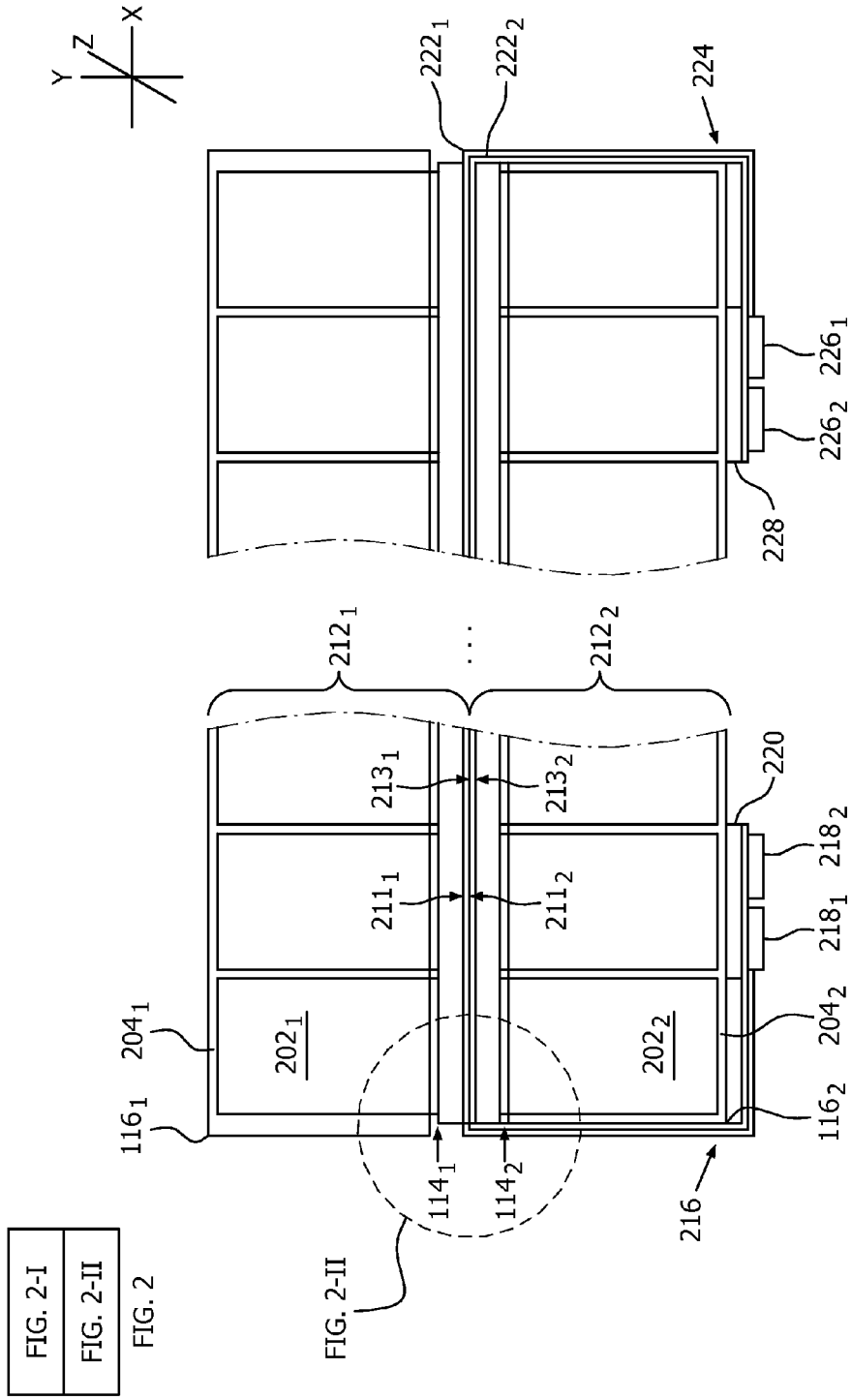
FIG. 2 illustrate an example of the multi-spectral imaging detector in which scintillator/photosensor pairs are arranged in a same spatial orientation.

FIG. 2 illustrates an example of a portion the detector array 110. For clarity and explanatory purposes, N=M=2. In this example, both of the photosensor array layers 114 are disposed between the two scintillator array layers 116.

A first scintillator array layer $116_1$ includes a two-dimensional (2D) array of first scintillator dixels (also referred to as scintillator pixels) $202_1$ (the dimension along the z-axis is not visible in FIG. 2). The first scintillator dixels $202_1$ include a lower atomic number Z material such as zinc selenide doped with titanium (ZnSe:Ti), yttrium-gadolinium aluminum garnet doped with cerium (YGAG:Ce), and/or other material which absorbs lower energy "soft" x-ray photons and emits light indicative thereof.

A first photosensor array layer $114_1$ includes a two-dimensional (2D) array of first photodiodes $206_1$ (the dimension along the z-axis is not visible in FIG. 2) mounted on an optional first substrate $208_1$. In a configuration in which the first substrate $208_1$ is omitted, the two-dimensional (2D) array of second photodiodes $206_1$ may be mounted directly upon a first circuit $210_1$, which is discussed in greater detail below. An example of a suitable material is one where the direct-conversion current from the radiation incident on the first photosensor array layer $114_1$ is no more than 0.1% of the signal current generated in the photosensor layer by light emitted from the scintillator. Such a material may have a thickness of thirty microns (30 μm) or less and/or include an organic material or a material with Z<35.

By way of example, in one instance, the first photosensor array layer $114_1$ is a thinned semiconductor-on-insulator (SOI) photodiode array with a silicon (Si), gallium arsenide (GaAs), etc. photodiode mounted directly on film such as a plastic or polyimide (PI) sheet. In another embodiment, the first photosensor array layer $114_1$ is a thin photodiode array (e.g., copper indium gallium (di) selenide (CIGS) or organic) printed on a flexible plastic sheet. Organic photodiodes (OPD's) with only lower Z elements (e.g., H, $C_6$, O, etc.) can be as thin as 1μ with low x-ray absorption.

The first scintillator array layer $116_1$ and the first photosensor array layer $114_1$ are coupled together with each first scintillator dixel $202_1$ optically coupled to a corresponding one of the first photodiodes $206_1$. Each of the first scintillator dixels $202_1$ is surrounded on five (5) of six (6) sides with a first reflective material $204_1$, which re-directs light traversing away from the first photodiode $206_1$ towards the first photodiode $206_1$.

The first circuit $210_1$ includes first and second sides $211_1$ and $211_2$, and a portion of the first side $211_1$ is electrically coupled to the first photodiodes $206_1$. In one instance, the first circuit $210_1$ is a thin plastic flexible circuit, and the signals output by the first photodiodes $206_1$ are routed from the individual first photodiodes $206_1$ and out of the first photosensor array layer $114_1$.

The first scintillator array layer $116_1$, the first photosensor array layer $111_1$, and the first circuit $210_1$ form a first assembly $212_1$.

A second scintillator array layer $116_2$ includes a two-dimensional (2D) array of second scintillator dixels $202_2$ (the dimension along the z-axis is not visible in FIG. 2). The second scintillator dixels $202_2$ include a higher atomic number Z material such as gadolinium oxysulfide (GOS), lutetium aluminum garnet (LuAG), and/or other material which absorbs higher energy "hard" x-ray photons and emits light indicative thereof A second photosensor array layer $114_2$ includes a two-dimensional (2D) array of second photodiodes $206_2$ (the dimension along the z-axis is not visible in FIG. 2) mounted on an optional second substrate $208_2$. In a configuration in which the second substrate $208_2$ is omitted, the two-dimensional (2D) array of second photodiodes $206_2$ may be mounted directly to a second circuit $210_2$, which is discussed in greater detail below.

The second photosensor array layer $114_2$ may be similar to the first photosensor array layer $114_1$ in that it includes a material where no more than 0.1% of the signal current generated in the photosensor layer is from light emitted from the scintillator. However, the thickness and/or material of the second photosensor array layer $114_2$ does not have to be the same as the thickness and/or material of the first photosensor array layer $114_1$. By using the same thickness and material for both the first photosensor array layer $114_1$ and the second photosensor array layer $114_2$, the behavior and response of the first photosensor array layer $114_1$ and the second photosensor array layer $114_2$ will be about the same, which may facilitate processing the signals, for example, where the signals are subtracted and/or otherwise combined.

The second scintillator array layer $116_2$ and the second photosensor array layer $114_2$ are coupled together, with each second scintillator dixel $202_2$ optically coupled to a different one of the second photodiodes $206_2$. Each of the second scintillator dixels $202_2$ is surrounded on five (5) of six (6) sides with a second reflective material $204_2$, which re-directs light traversing away from the second photodiode $206_2$ towards the second photodiode $206_2$.

The second circuit $210_2$ includes first and second sides $213_1$ and $213_2$ and a portion of the first side $213_1$ is electrically coupled to the second photodiodes $206_2$. Likewise, in one instance, the second circuit $210_2$ is a thin plastic flexible circuit, and the signals output by the individual second photodiodes $206_2$ are routed from the individual second photodiodes $206_2$ and out of the second photosensor array layer $114_2$.

The second scintillator array layer $116_2$, the second photosensor array layer $114_2$, and the second circuit $210_2$ form a second assembly $212_2$.

The second side $211_2$ of the first circuit $210_1$ and the first side $213_1$ of the second circuit $210_2$ are coupled together, coupling the first assembly $212_k$ and the second assembly $212_2$ together.

First electrical conducting ends $214_1$ and $214_2$ of the first and second circuits $210_1$ and $210_2$ wrap around a first side $216$ the second scintillator array layer $116_2$ and are electrically coupled to first readout integrated circuits $218_1$ and $218_2$ mounted to a first radiation shield $220$ affixed to the second reflective material $204_2$. The first radiation shield $220$ shields the first readout integrated circuits $218_1$ and $218_2$ from residual radiation traversing the second scintillator array layer $116_2$.

Second electrical conducting ends $222_1$ and $222_2$ of the first and second circuits $210_1$ and $210_2$ wrap around a second opposing side $224$ of the second scintillator array layer $116_2$ and are electrically coupled to second readout integrated circuits $226_1$ and $226_2$ mounted to a second radiation shield $228$ affixed to the second reflective material $204_2$. The second radiation shield $228$ shields the second readout integrated circuits $226_1$ and $226_2$ from residual radiation traversing the second scintillator array layer $116_2$.

The radiation shields $220$ and $228$ may include tungsten, bismuth oxide composite resin, and/or other material with x-ray attenuation characteristics which will inhibit x-ray photons from reaching the circuits $218_1$ and $218_2$ and the circuits $226_1$ and $226_2$. In a variation, at least one of the readout integrated circuits $218_1$ and $218_2$ and the circuits $226_1$ and $226_2$ includes radiation-hardened components. In this variation, the portion of radiation shields $220$ and $228$ corresponding to the readout integrated circuit with the radiation-hardened components can be omitted.

In a variation of the above, only a single readout integrated circuit (e.g., $218_1$, $226_1$, or other) is used in connection with the first photosensor array layer $114_1$, and either or both of the first or second electrical conducting ends $214_1$ and $222_k$ are used to route signal from the first photosensor array layer $114_1$ to the single readout integrated circuit. Where only one of the first or second electrical conducting ends $214_1$ and $222_1$ are used, the other of the first or second electrical conducting ends $214_1$ and $222_1$ can be omitted.

Likewise, a single readout integrated circuit only (e.g., $218_2$, $226_2$, or other) may be used in connection with the second photosensor array layer $114_2$, and either or both of the first or second electrical conducting ends $214_2$ and $222_2$ are used to route signal from the second photosensor array layer $114_2$ to the single readout integrated circuit. Where only one of the first or second electrical conducting ends $214_2$ and $222_2$ are used, the other of the first or second electrical conducting ends $214_2$ and $222_2$ can be omitted.

In yet another variation, a single readout integrated circuit (e.g., $218_1$, $226_1$, $218_1$, $226_2$, or other) is used for both of the first and second photosensor array layers $114_1$ and $114_2$. In still another variation, more than two readout integrated circuits can be used with one or both of the first and second photosensor array layers $114_1$ and $114_2$.

In the illustrated configuration, both the first photosensor array layer $114_1$ and the second photosensor array layer $114_2$ are located between the first scintillator array layer $116_1$ and the second scintillator array layer $116_2$, and the detector array $110$ is installed in the system $100$ such that the first scintillator array layer $116_1$ receives incident radiation and the second scintillator array layer $116_2$ receives radiation that traverses the first scintillator array layer $116_1$.

Figure 3:
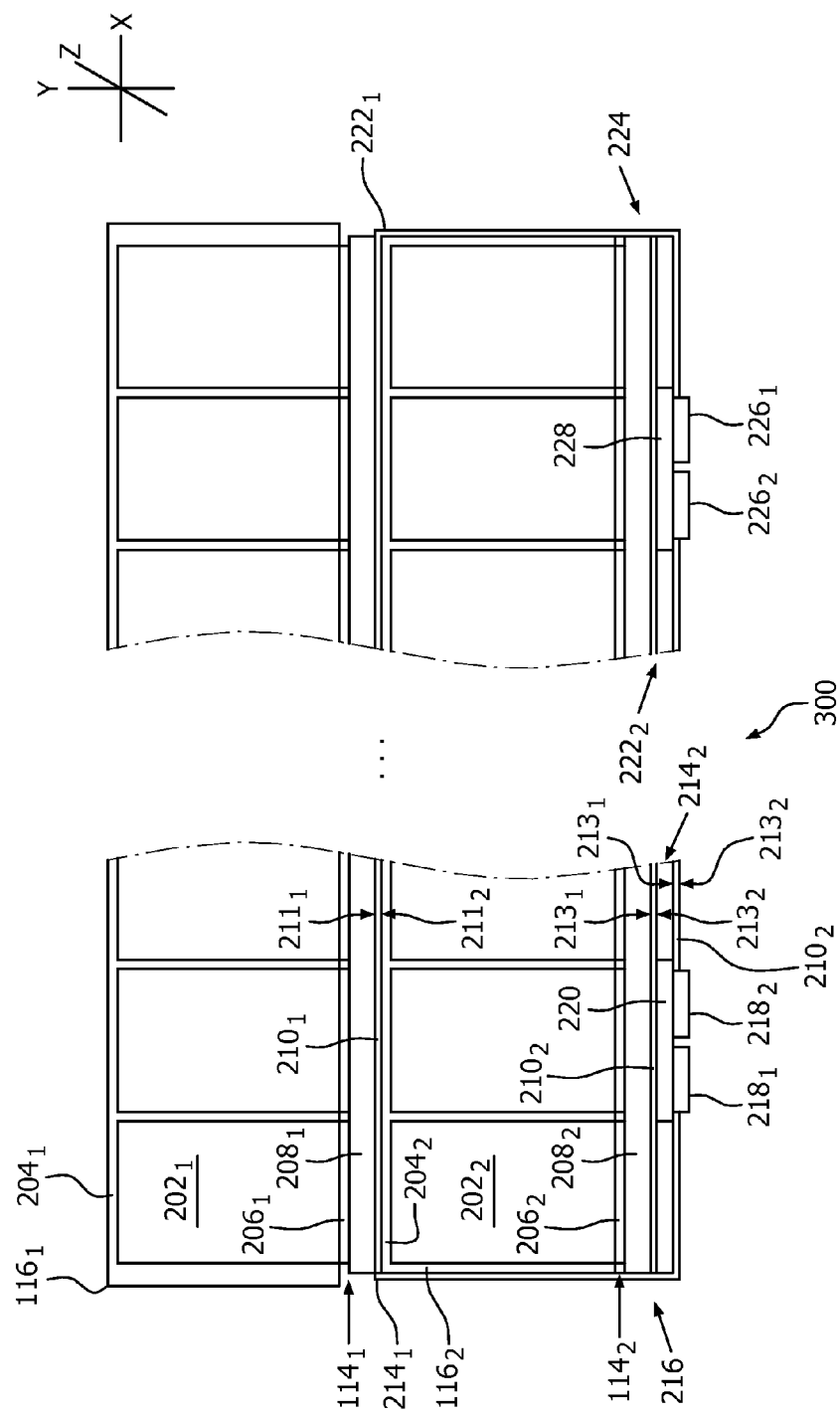
FIG. 3 illustrate an example of the multi-spectral imaging detector in which scintillator/photosensor pairs are arranged in a reverse spatial orientation.

FIG. 3 is structurally similar to FIG. 2 except that the second assembly $212_2$ is flipped one hundred and eighty degrees, the second side $211_2$ of the first circuit $210_1$ is coupled with the second scintillator array layer $116_2$, and the first and second ends $214_2$ and $222_2$ do not wrap around the first and second ends $216$ and $224$ of the second scintillator array layer $116_2$, but instead fold and wrap back around within a center region $300$ and lead back to the readout integrated circuits $218_2$ and $226_2$.

FIGS. 4 and 5 are structurally similar to FIG. 2 except that the first photosensor array layer $114_1$ includes electrically conductive pathways (not visible) that route signals produced by the first photodiodes $206_1$ to one or more edges $400$ of the a first substrate $208_1$. In addition, the second photosensor array layer $114_2$ is a back-illuminated photodiode (BIP). Furthermore, the first and second assemblies $212_1$ and $212_2$ are coupled via an adhesive or solder by direct flip-chip. Moreover, the first and second circuits $210_1$ and $210_2$ are omitted, and the second assembly $212_2$ is coupled to a substrate $400$.

In FIG. 4, electrical interconnects $402$ are coupled to the electrically conductive pathways from a side $404$ of the substrate $208_1$ facing the first scintillator array layer $116_1$ and wrap around the first scintillator array layer $116_1$ and are electrically connected to the substrate $400$. In FIG. 5, electrical interconnects $402$ are coupled to the electrically conductive pathways from an opposing side $500$ of the substrate $208_1$, which faces the second scintillator array layer $116_2$, and wrap around the first scintillator array layer $114_1$ and are electrically connected to the substrate $400$.

In both FIGS. 4 and 5, the outputs of the individual second photodiodes $206_2$ are electrically coupled to the substrate $400$ through electrically conductive vias (not visible) in the second photosensor array layer $114_2$ and electrically conductive contacts $408$. The outputs from both sets of photodiodes $206_1$ and $206_2$ are further routed to the readout electronics $406$ through electrically conductive vias (not visible) in the substrate $400$ and electrically conductive pads (not visible) of the substrate $400$ and the readout integrated circuit $406$.

In this embodiment, the readout integrated circuit $406$ includes radiation-hardened components. In an alternative embodiment, a radiation shield similar to the radiation shield $220$ or $228$ of FIG. 2 is disposed between the substrate $400$ and the readout integrated circuit $406$. In such an embodiment, the readout integrated circuit $406$ may or may not include radiation-hardened components.

FIG. 6 shows a variation of FIG. 5 for the readout integrated circuit. It is to be appreciated that this variation can also be used with one or more of the embodiments discussed in FIGS. 2-4. In this variation, a first radiation shield $600$ is disposed between the substrate $400$ and first readout integrated circuit $602$ for the second assembly $212_2$. First electrically conductive connections 604 route the signals from the second assembly 212₂ to the first readout integrated circuit 602.

The electrically conductive connections 604 also provide support for a second substrate 606, which supports a second radiation shield 608 that is disposed between the second substrate 606 and second readout integrated circuit 610 for the first assembly 212₁. The electrical interconnects 402 route signals from the first assembly 212₁ to the second substrate 606, and second electrically conductive connections 612 route signals from the second substrate 606 to the second readout integrated circuit 610.

FIG. 7 illustrate a method of using the embodiments discussed in connection with FIGS. 1-6 and/or variations thereof.

At 702, radiation emitted by the radiation source 108 illuminates a first scintillator array layer of the scintillator array layer 116 closest to the examination region 106.

At 704, the first scintillator array layer absorbs a first portion of the radiation and emits first light in response thereto.

At 706, corresponding first photosensor array layer receives the first light and produces a first output signal.

At 708, a second scintillator array layer of the scintillator array layer, which is father from the examination region 106 relative the first scintillator array layer absorbs a second portion of the radiation, which traverses the first scintillator array layer and the first photosensor array layer, and emits second light in response thereto.

At 710, corresponding second photosensor array layer receives the second light and produces a second output signal.

At 712, the first and second output signal are routed to corresponding readout electronics, which route the first and second output signals for processing.

It is to be appreciated that the ordering of the above acts is not limiting. As such, other orderings are contemplated herein. In addition, one or more acts may be omitted and/or one or more additional acts may be included.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:
1. An imaging system comprising:
a radiation sensitive detector array, comprising:
a first assembly including:
a first scintillator array layer;
a first photosensor array layer optically coupled to the first scintillator array Layer; and
a first circuit electrically connected to the first photosensor array layer;
a second assembly including:
a second scintillator array layer;
a second photosensor array layer optically coupled to the second scintillator array layer; and
a second circuit electrically connected to the second photosensor array layer; and
a readout circuit affixed to the second scintillator,
wherein the first assembly and the second assembly are stacked in opposing directions, the first circuit is affixed to the second circuit, the second circuit is electrically connected to the readout integrated circuit by a first flexible connection that runs along a side of the second scintillator, and the first circuit is electrically connected to the readout integrated circuit by a second flexible electrical connection that runs along the side.

2. The imaging system of claim 1, wherein the first photosensor array layer and the second photosensor array layer are located between the first scintillator array layer and the second scintillator array layer.

3. The imaging system of claim 1, wherein the first photosensor array layer or the second photosensor array layer produces a first current by direct conversion that is less than one tenth of one percent of a second current produced in the first photosensor array layer or the second photosensor array layer by light from the first scintillator array layer or the second scintillator array layer.

4. The imaging system of claim 3, wherein the first photosensor array layer and the second photosensor array layer include a material with an atomic number of less than thirty-five.

5. The imaging system of claim 3, wherein the first photosensor array layer and the second photosensor array layer comprises at least one of silicon or gallium arsenide.

6. The imaging system of claim 5, wherein the first photosensor array layer and the second photosensor array layer include a thinned semiconductor-on-insulator photodiode array mounted on film.

7. The imaging system of claim 5, wherein the first photosensor array layer and the second photosensor array layer include a thin photodiode array printed on a flexible plastic sheet.

8. The imaging system of claim 1, wherein the first scintillator array layer is nearer to incoming radiation than the second scintillator array layer, wherein the first scintillator array layer includes a first material with a first atomic number and the second scintillator array layer that is farther from the incoming radiation than the first scintillator array layer includes a second material with a second atomic number material, wherein the first atomic number is less than the second atomic number.

9. The imaging system of claim 8, wherein the first scintillator array layer includes at least one of doped zinc selenide or doped yttrium-gadolinium aluminum garnet.

10. The imaging system of claim 8, wherein the second scintillator array layer includes at least one of gadolinium oxysulfide or lutetium aluminum garnet.

11. The imaging system of claim 1, wherein the first photosensor array layer and the second photosensor array layer, comprises: individual photodiodes.

12. The imaging system of claim 11, further comprising:
second readout electronics; and
a second electrical circuit coupled to the second photosensor array layer, wherein the second electrical circuit routes electrical signals produced by a subset of the individual photodiodes to the second readout electronics.

13. A method comprising:
detecting radiation with a multi-spectral horizontal detector array of an imaging system wherein the detector array includes:
a first assembly including:
a first scintillator array layer;
a first photosensor array layer optically coupled to the first scintillator array layer; and
a first circuit electrically connected to the first photosensor array layer;
a second assembly including:
a second scintillator array layer;
a second photosensor array layer optically coupled to the second scintillator array layer; and a second circuit electrically connected to the second photosensor array layer; and a readout circuit affixed to the second scintillator, wherein the first assembly and the second assembly are stacked in opposing directions, the first circuit is affixed to the second circuit, the second circuit is electrically connected to the readout integrated circuit by a first flexible connection that runs along a side of the second scintillator, and the first circuit is electrically connected to the readout integrated circuit by a second flexible electrical connection that runs along the side.

14. The method of claim 13, wherein the first photosensor array layer and the second photosensor array layer convert less than one percent of radiation incident thereon into direct-conversion current.

15. The method of claim 14, wherein the first photosensor array layer and the second photosensor array layer include a material with an atomic number of less than thirty-five.

16. The method of claim 13, further comprising:
routing signals from individual photodiodes of the first photosensor array layer and the second photosensor array layer to readout electronics using flexible electrical circuits.

17. The method of claim 16, further comprising:
routing the signals to at least two integrated circuits of the readout electronics which are arranged with respect to each other along a first direction of incoming radiation.

18. The method of claim 16, further comprising:
routing the signals to at least two integrated circuits of the readout electronics which are arranged with respect to each other along a second direction transverse to incoming radiation.

19. The method of claim 16, further comprising:
routing the signals to readout electronics that includes radiation hardened components.

20. The method of claim 16, further comprising:
shielding radiation traversing the first scintillator array layer, the second scintillator array layer, the first photosensor array layer, and the second photosensor layer with a radiation shield located between the readout electronics and the radiation.

21. The method of claim 13, further comprising:
routing signals produced by individual photodiodes of the first photosensor array layer and the second photosensor array layer from at least one edge of the first photosensor array layer and the second photosensor array layer to readout electronics using an electrical interconnect.

22. A radiation sensitive detector array, comprising:
a first assembly including:
   a first scintillator array layer;
   a first photosensor array layer optically coupled to the first scintillator array layer; and
   a first circuit electrically connected to the first photosensor array layer;
a second assembly including:
   a second scintillator array layer;
   a second photosensor array layer optically coupled to the second scintillator array layer; and
   a second circuit electrically connected to the second photosensor array layer; and
a readout circuit affixed to the second scintillator,
wherein the first assembly and the second assembly are stacked in opposing directions, the first circuit is affixed to the second circuit, the second circuit is electrically connected to the readout integrated circuit by a first flexible connection that runs along a side of the second scintillator, and the first circuit is electrically connected to the readout integrated circuit by a second flexible electrical connection that runs along the side.

* * * * *